(12) United States Patent
Chary et al.

(10) Patent No.: US 11,566,233 B2
(45) Date of Patent: Jan. 31, 2023

(54) THREE-DIMENSIONAL IN VITRO LUNG MODEL, PROCESS FOR PREPARING SAID MODEL, AND ITS USE FOR DETERMINING AND /OR PREDICTING THE SENSITIZING EFFECTS OF INHALABLE PRODUCTS

(71) Applicant: LUXEMBOURG INSTITUTE OF SCIENCE AND TECHNOLOGY, Esch-sur-Alzette (LU)

(72) Inventors: Aline Chary, Audun-le-Tiche (FR); Arno Gutleb, Remich (LU); Tommaso Serchi, Kirsch-les-Sierck (FR); Brunhilde Blomeke, Pluwig (DE)

(73) Assignee: LUXEMBOURG INSTITUTE OF SCIENCE AND TECHNOLOGY, Esch-sur-Alzette (LU)

( * ) Notice: Subject to any disclaimer, the term of this patent is extended or adjusted under 35 U.S.C. 154(b) by 611 days.

(21) Appl. No.: 16/472,335

(22) PCT Filed: Dec. 26, 2017

(86) PCT No.: PCT/EP2017/084583
§ 371 (c)(1),
(2) Date: Jun. 21, 2019

(87) PCT Pub. No.: WO2018/122219
PCT Pub. Date: Jul. 5, 2018

(65) Prior Publication Data
US 2019/0376048 A1 Dec. 12, 2019

(30) Foreign Application Priority Data
Dec. 27, 2016 (LU) .......................................... 93401

(51) Int. Cl.
*C12N 5/071* (2010.01)
*C12N 5/0784* (2010.01)
*G01N 33/50* (2006.01)

(52) U.S. Cl.
CPC ......... *C12N 5/0697* (2013.01); *C12N 5/0639* (2013.01); *C12N 5/0688* (2013.01);
(Continued)

(58) Field of Classification Search
CPC .. C12N 5/0697; C12N 5/0639; C12N 5/0688; C12N 2502/1114; C12N 2502/1121;
(Continued)

(56) References Cited

U.S. PATENT DOCUMENTS

2009/0075282 A1 3/2009 Mahmood et al.

OTHER PUBLICATIONS

Klein et al., An improved 3D tetraculture system mimicking the cellular organization at the alveolar barrier to study the potential toxic effects of particles on the lung. Particle and Fibre Toxicology, vol. 10 (2013) article 31. (Year: 2013).*

(Continued)

*Primary Examiner* — Kara D Johnson
(74) *Attorney, Agent, or Firm* — Ipsilon USA, LLP

(57) ABSTRACT

The invention relates to a three-dimensional in vitro alveolar lung model comprising essentially the four cells types as follows: alveolar type II epithelial cells able to secrete (lung laying) surfactant, endothelial cells which forms the inner lining of capillaries providing a permeable barrier, dendritic-like cells, such as non-differentiated THP-1, linking innate and adaptive immunity and macrophage-like cells, able to participate to defense mechanisms by ingesting foreign materials by phagocytosis.

The invention also relates to a process for preparing said model, and its use for assessing the irritation potential or toxicity of inhalable products such as particles or molecules on the alveolar barrier of lungs, and also for determining and/or predicting the sensitizing effects of inhalable products such as particles or molecules on the alveolar barrier of lungs.

18 Claims, 10 Drawing Sheets

(52) U.S. Cl.
CPC ............... *C12N 2502/1114* (2013.01); *C12N 2502/1121* (2013.01); *C12N 2502/1157* (2013.01); *C12N 2502/27* (2013.01); *C12N 2502/28* (2013.01); *C12N 2503/04* (2013.01); *G01N 33/5088* (2013.01)

(58) Field of Classification Search
CPC ........ C12N 2502/1157; C12N 2502/27; C12N 2502/28; C12N 2503/04; G01N 33/5088
See application file for complete search history.

(56) References Cited

OTHER PUBLICATIONS

Sebastian G Klein et al: "An improved 3D tetraculture system mimicking the cellular organisation at the alveolar barrier to study the potential toxic effects of particles on the lung" Particle and Fibre Toxicology, Jan. 1, 2013.

L. Muller et al: "Oxidative stress and inflammation response after nanoparticle exposure: differences between human lung _ cell monocultures and an advanced three-dimensional model of the human epithelial airways", Journal of the Royal Society. Interface Jul. 8, 2009.

Carsten Schleh et al: "Surfactant Protein D modulates allergen particle uptake and inflammatory response in a human epithelial airway model", Respiratory Research, Biomed Central Ltd., Feb. 1, 2012.

Cristian E De Souza Carvalho et al: "Carrier interactions with the biological barriers of the lung: Advanced in vitro models and challenges for pulmonary drug delivery," Advanced Drug Delivery Reviews, Aug. 1, 2014.

E. Alfaro-Moreno et al: "Co-cultures of multiple cell types mimic pulmonary cell communication in response to urban PM10" European Respiratory Journal., Nov. 1, 2008.

Search Report dated Jan. 31, 2017.
International Search Report dated Feb. 26, 2018.

\* cited by examiner

THREE-DIMENSIONAL IN VITRO LUNG MODEL, PROCESS FOR PREPARING SAID MODEL, AND ITS USE FOR DETERMINING AND /OR PREDICTING THE SENSITIZING EFFECTS OF INHALABLE PRODUCTS

RELATED APPLICATION

This application is a National Phase of PCT/EP2017/084583 filed on Dec. 26, 2017, which claims the benefit of priority from Luxembourg Patent Application No. 93401, filed on Dec. 27, 2016, the entirety of which are incorporated by reference.

FIELD OF THE INVENTION

The present invention relates to a three-dimensional in vitro alveolar lung model and to the process for preparing said model.

The invention also relates to the use and process thereof, for assessing the irritation potential or toxicity of inhalable products such as particles or molecules on the alveolar barrier of lungs, and also for determining and/or predicting the sensitizing effects of inhalable products such as particles or molecules on the alveolar barrier of lungs.

BACKGROUND OF THE INVENTION

Respiratory sensitization as a consequence of exposure to chemical products has increased over the last decades, leading to an increase of morbidity. The broader use of synthetic compounds, e.g. fragrances and industrial solvents, resulted in an exponential growth of substances to which we are potentially daily exposed. Some of these substances are known to induce respiratory sensitization, meaning that they can trigger the development of allergy over time, with potential adverse systemic effects.

This may lead to respiratory diseases such as asthma, allergic rhinitis, rhino-conjunctivitis and sinusitis.

In order to characterize the potential risks of these chemicals, it is necessary to fully understand the mechanisms involved in lung sensitization.

In the past, animal studies provided useful results for the understanding of mechanisms involved in the development of respiratory allergies. However, the mechanistic understanding of the cellular effects involved is still limited. Several methods have been proposed to discriminate and identify functional and structural features of an allergen, but none of these studies led to conclusive results mainly due to biogenic and environmental confounding cofactors. This lack of knowledge hampers the development of predictive in vitro models, leaving in vivo models as the unique tool for the characterization respiratory allergens. However, despite the lack of validated methods to identify and characterize respiratory sensitizers, regulations such as REACH (Registration, Evaluation, Authorization and Restriction of Chemicals) require and encourage the use of non-animal methods for toxicology assessment.

Currently, there is no validated in vitro method, which could be used as an alternative to in vivo testing, which would be able to identify and characterize the potential of chemicals acting as respiratory sensitizers.

In a publication of 2013 (Klein et al Particle and Fibre Toxicology, 2013, 10:31) the authors proposed a tetraculture model composed of an alveolar type II epithelial cell line (A459), differentiated macrophage-like cells (THP-1), mast cells (HMC-1) and endothelial cells (EA.hy 926), which made it possible that the model can then be exposed at the air-liquid interface (ALI). However, it was observed that the cells formed heterogeneous colonies under submerged conditions: this leads to overestimation of observed effects in the results for instance for ROS (Reactive oxygen species) production and IL-8 secretion. Furthermore, Klein's model cannot be used for the evaluation of sensitizing effects due to the lack of relevant competent cells and does not allow for cell migration through the membrane, due to the reduced pores size. The exposure at the ALI has a priming effect on the culture, which presents higher basal levels of oxidative stress, as compared to the incubator controls. This results in a more physiological answer to external challenges that provides a more realistic estimation of the toxicological effects. In addition, the exposure at the ALI allows the realistic exposure to exogenous compounds without prior dilution in cell culture medium, which contains many biological molecules that will interact with the chemicals under investigation, thus possibly altering the readout of biological effects leading to unpredictable under- or over-estimation of the biological effects.

All the previous models so far proposed for respiratory toxicology generally made use of bronchial cell lines, not relevant in the context of respiratory sensitization. Therefore, there is a need for a relevant tool to study respiratory sensitization and for predicting the respiratory potential of inhalable chemicals and small particles.

AIM OF THE INVENTION

A first object of the invention is to provide an in vitro model to mimic the alveolar surface of the lungs, in order to assess the respiratory sensitization potential of inhalable products, chemicals as well as particles.

SUMMARY OF THE INVENTION

The present invention relates to a three-dimensional in vitro alveolar lung model comprising mainly the four cell types as follows:

a) alveolar type II epithelial cells able to secrete (lung laying) surfactant, b) endothelial cells which form the inner lining of capillaries providing a permeable barrier, c) dendritic-like cells, (linking innate and adaptive immunity), d) macrophage-like cells, able to participate to defense mechanisms by ingesting foreign materials by phagocytosis, wherein:

said three-dimensional in vitro alveolar lung model is in the form of a culture well equipped with a porous membrane separating the well into an apical compartment exposed to an air-liquid interface, and a basolateral compartment submerged in a culture medium, said epithelial cells and said macrophages being present in the apical compartment, and said endothelial cells and said dendritic-like cells being present at the basolateral compartment and immerge in the culture medium, said porous membrane has pores comprised between 2 and 10 µm, allowing possible migration of the dendritic-like cells from the basolateral compartment to the apical compartment.

By "mainly" is meant here that said alveolar lung model comprises essentially the four cells type above, in particular said alveolar lung model does not include mast cells, which could lead to false results.

By "essentially", is in particular meant that said model does not include mast cells, that could lead to false results in the assessment of the toxicity or sensitizing effects of inhalable products.

DETAILED DESCRIPTION OF THE INVENTION

More particularly, the macrophage-like cells are THP-1 cells, differentiated with PMA (Phorbol-12-myristate-13-acetate) or with 1,25-dihydroxyvitamin D3, preferably differentiated with PMA. This differentiation is preferably performed during several days: advantageously 3 to 10 days, and preferably 5 days.

In the model of the present invention, all cells are immortalized mammalian cell lines, which are cells more stable than primary cells, and are preferably immortalized human cell lines.

"Preferably", said alveolar type II epithelial cells are A549 cells.

Also "preferably", said endothelial cells are EA.hy926 cells.

And also "preferably", said dendritic-like cells are non-differentiated THP-1 cells, which are well established models for human dendritic cells.

Dendritic cells are of central importance in the sensitizing process, since these cells are deputed to recognition and capture antigen, which triggers the immune response.

Advantageously, the three-dimensional in vitro alveolar lung model of the invention comprises:
a) A549 cells, as alveolar type II epithelial cells,
b) EA.hy926 cells, as endothelial cells
c) non-differentiated THP-1 cells, as dendritic-like cells,
d) THP-1 cells, differentiated with PMA, as macrophage-like cells, and excludes mast cells.

In a preferred embodiment of the invention, the three-dimensional in vitro alveolar lung model of the invention consists exclusively of the following tetraculture:
a) A549 cells, as alveolar type II epithelial cells,
b) EA.hy926 cells, as endothelial cells
c) non-differentiated THP-1 cells, as dendritic-like cells,
d) THP-1 cells, differentiated with PMA, as macrophage-like cells.

Compared to the tetraculture model of Klein 2013, the present model excludes mast cells that could change the local microenvironment and influence the response of the dendritic-like cells. Therefore, the present model mimics more precisely the in vivo situation, where mast cells are only present during the step of allergic inflammation (elicitation phase) but not during the sensitization phase which precedes the allergic inflammation. Mast cells are responding to various biological stimuli, of which the most important is the release of Immunoglobulin E (IgE) by the B-lymphocytes. As B-lymphocytes are not present in the model of the present invention and, moreover, the HMC-1 cells, do not present a functional receptor for IgE, the inclusion of mast cells in the present model would only add unnecessary complexity without bringing any additional value.

The porous membrane separating the apical and the basolateral compartments may be part for instance of a Transwell® insert.

Advantageously, the porous membrane has pores comprised between 3 and 8 µm, more preferably between 4 and 6 µm. In Klein's model, dendritic cells were absent from the tetraculture, and of course, could not be present in the apical compartment. The absence of dendritic cells in Klein's model made for that model impossible to predict respiratory sensitization. Dendritic cells are pivotal in the induction phase of the sensitization process and in their absence the entire process cannot be studied.

The ability for the dendritic-like cells to migrate from the basolateral compartment to the apical compartment is also an important feature of the model (which was not possible in Klein's model). Dendritic cells are naturally not present in the alveoli, to which they are recruited only as a consequence of exogenous stimuli. Also, in order to get realistic estimation of the sensitizing potential, it is important, that the dendritic-like cells are not directly exposed to the sensitizing agents, which should first enter in contact with the epithelium and the resident macrophages. This contact might enhance or reduce the sensitizing potential of inhaled substances due to metabolic process by epithelial cells or macrophages.

The present invention also relates to a process for preparing the above three-dimensional in vitro alveolar lung model, comprising co-culture of cells a)-d) in an insert having a porous membrane, in the following step sequence:
i) seeding the lower face (which will become the basolateral side) of a membrane insert having pores comprised between 2 and 10 µm with $0.24 \cdot 10^5$ to $0.6 \cdot 10^5$ endothelial cells/cm$^2$,
ii) at least four hours later, seeding the other side (apical side) of the membrane insert with the alveolar type II epithelial cells, preferably $0.12 \cdot 10^5$ to $1.2 \cdot 10^5$, preferably $0.5 \cdot 10^5$ to $1.0 \cdot 10^5$ cells/cm$^2$,
iii) about 4 days later, adding a cell suspension containing between 0.1 and one million dendritic-like cells/mL to the basolateral side of the membrane insert, and then
iv) adding macrophage-like cells on top of the alveolar type II epithelial cells seed, preferably $0.12 \cdot 10^5$ to $1.2 \cdot 10^5$ macrophage-like cells/cm$^2$, and finally,
v) introduce the membrane insert in a medium in order that said endothelial cells and said dendritic-like cells are (present at the basolateral compartment) immerged in the co-culture medium, and said epithelial cells and said macrophages-like are present in the apical compartment, at the air-liquid interface (ALI).

Preferably in the above process, said macrophage-like cells are THP-1 cells, differentiated with PMA (Phorbol-12-myristate-13-acetate), and/or said alveolar type II epithelial cells are A549 cells, and/or said endothelial cells are EA.hy926 cells, and/or said dendritic-like cells are non-differentiated THP-1 cells.

The three-dimensional in vitro alveolar lung model of the present invention finds interesting applications, in particular:
use for assessing the irritation potential or toxicity of inhalable products such as particles or molecules on the alveolar barrier of lungs;
use for determining and/or predicting the sensitizing effects of inhalable products such as particles or molecules on the alveolar barrier of lungs.

The present invention also relates to a process for determining and/or predicting the sensitizing effects, and/or the irritation potential or toxicity, of inhalable products such as particles or molecules on the alveolar barrier of lungs, comprising:
A) a step of exposing by pulverizing/nebulizing the inhalable product to be tested over the apical compartment of the three-dimensional in vitro alveolar lung model according to anyone of claims 1 to 8 in the form of a culture well equipped with a porous membrane having pores comprised between 2 and 10 µm, said epithelial cells and said macrophages being present at the apical side of the membrane, and said endothelial cells and said dendritic-like cells being present at the basal side of the membrane, said endothelial cells and said dendritic-like cells being immerged in the co-culture medium, said exposing leading to activation of the dendritic-like cells, B) a step of co-culturing said activated dendritic-like cells with a T lymphoblast cell line.

Preferably, T-cells should present a Helper type 2 (TH2) profile if the product to be tested is a suspected respiratory sensitizer.

Markers for the respiratory sensitization potential may be measured by FACS (such as for example CD40, CD54, CD86, TSLPr, IL-1ra, OX40L) and/or by ELISA (TSLP, IL-33, IL-25, RANTES, MCP-1, MIP-3a, IL-6, IL-7, IL-10 and GM-CSF).

Further biological endpoints, such as release of interleukins, genotoxicity, biomarkers of sensitization, proteomics, transcriptomics, metabolic activation may also be measured.

The three-dimensional in vitro alveolar lung model of the invention presents the main following advantages:
  Absence of mast cells, that could induce false results;
  Possibility of exposure at the air-liquid interface (ALI), using gases, liquids or powders as materials to be tested;
  Possibility of testing chemicals and particles for both aspects: their inflammatory or sensitizing potential, contrary to the Klein et al. 2013 model that can only be used for irritation potential;
  Possibility of measuring a multitude of biological endpoints (e.g. release of interleukins, genotoxicity, biomarkers of sensitization, proteomics, transcriptomics, metabolic activation, etc.).

FIGURES

Further advantages and aspects of the lung model of the invention could be deducted from the description of the embodiments presented in the example part below, with reference to the accompanying drawings, in which.

EXAMPLES

Example 1

In this example are used the following cell lines: A549, EA.hy926, THP-1 and Mϕ-THP-1. Their respective characteristics are as follows:
  Cell line A549 corresponds to Human bronchial epithelial cells with ability to produce surfactant;
  EA.hy926 cell line is a somatic cell hybrid with endothelial characteristics;
  THP-1 is a human monocytic leukemic cell line; and
  Mϕ-THP-1 are macrophages derived from THP-1 cells, differentiated with PMA (Phorbol-12-myristate-13-acetate) or with 1,25-dihydroxyvitamin D3.

Preparation of the Different Media:

The protocols used are as follows:

EA.hy926 medium:
  Remove 60 mL of DMEM (Dulbecco's Modified Eagle's medium) medium from a new bottle (500 mL) and add 50 mL of FBS (10%), then 5 mL of HEPES stock solution (250 mM; sterile, filtered) to get a HEPES buffered medium (25 mM),
  Preservation with 5 mL Pen/Strep (penicillin/streptomycin).

Coculture 10% medium:
  Remove 5 mL of DMEM media from a new bottle (500 mL) and add 5 mL of HEPES stock solution (250 mM; sterile, filtered) to get a HEPES buffered medium (25 mM),
  Mix and remove 125 mL,
  Add 50 mL of IMDM, then add 75 mL of RPMI medium,
  Mix and remove 55 mL, Then add 50 mL of FBS (10%) into the medium and 5 mL of Pen/Strep.

Coculture 1% Medium:

Remove 5 mL of DMEM medium from a new bottle and add 5 mL of HEPES stock solution (250 mM; sterile, filtered) to get a HEPES buffered medium (25 mM), Mix and remove 125 mL, Add 50 mL of IMDM then add 75 mL of RPMI, Mix and remove 10 mL, Add 5 mL of FBS (1%) into the medium and 5 mL of Pen/Strep.

THP-1 Complete Medium:

Remove 57.5 mL of RPMI medium from a new bottle (500 mL). From those 52.5 mL, transfer 10 mL in a falcon tube and throw away the remaining medium, Prepare the working solution of 10 mM 3-mercapto ethanol in RPMI medium by adding 7 μL of commercial solution into 10 mL RPMI, mix, transfer 2.5 mL into the bottle of medium, Add 50 mL of FBS (10%) into the medium, then 5 mL of Pen/Strep.

Preparation of the Three-Dimensional In Vitro Alveolar Lung Model:

In this example, the chronology of the different steps was the following:

1. Day −2

Differentiating macrophage cells (overnight):

THP-1 cells are differentiated with PMA (Phorbol-12-myristate-13-acetate) or with 1,25-dihydroxyvitamin D3 (80 μLPMA+40 mL medium+16 million cells per flask T125) overnight and then kept in the flask for 1-5 days, medium being renewed overnight.

2. Day 0: Seeding of the Insert

Preparation of the EA.Hy926 Cells:

Add 0.11 million to 0.54 million cells per insert (0.24 $10^5$ to 0.6 $10^5$ cells/cm$^2$, preferentially 0.24 $10^5$ cells/cm$^2$), The volume needed for the seeding in the insert is here 700 μL, Prepare first the cell suspension for all inserts (+2 extra inserts for pipetting mistakes), mix in order to well homogenate the cell suspension, Properly put the inserts inside the well of the plate, Return the plate and gently put the 700 μL of EA.hy926 under the insert, Then place the plate into incubator.

At least 4 hours later:

Preparation of the A549 Cells:

The volume needed for the seeding in the insert is here 2 mL,

The pellet of A549 cells is re-suspended in the EA.hy926 medium: 0.27 million to 0.54 million cells per insert (0.12 $10^5$ to 1.2 $10^5$ cells/cm$^2$, preferentially 0.6 $10^5$ cells/cm$^2$), Prepare first the cell suspension of A549 cells for all inserts (into EA.hy926 medium, count 2 extra inserts for pipetting errors). Mix/homogenate well the cell suspension.

Prepare the plate with inserts for the seeding and homogenate the cell suspension from time to time when seeding cells on inserts, to avoid the cells settling down in the tube):

Return plate and add 1.5 mL of EA.hy926 medium into the well,

Check the endothelial cellular layer under microscope,

Add the 2 mL of A549 cells in the insert.

3. Day 3:

Changing the medium of the plate of inserts:

Remove old medium of the insert and add 2 mL of Coculture 10% medium,

Remove old medium of the well and add 2 mL of Coculture 10% medium,

4. Day 4:

Prepare DC-THP-1 in a 6-Well Plate:

Prepare cell suspension at 1 million of DC-THP-1 cells/mL in the present example (from 0.1 million cells to 1 million cells per mL).

Take a new plate and add 1 mL (i.e. a volume sufficient to recover the EA.hy926 cells) of DC-THP-1 cell suspension in the 6 wells of the new plate and move inserts from the old plate to the new one.

Differentiated THP-1 Cells (Mφ-THP-1):

Wash cells with PBS,

Add accutase on differentiated THP-1 cells to detach cells, and put the flask into incubator for 15 minutes, Centrifuge 5 minutes at 300 g, discard supernatant, Dissolve the pellet in Coculture 1%, Count the cells and add into the insert 0.27 to 0.54 million of MD-THP-1 cells per insert in the present example (0.12 to 1.2 $10^5$ cells/cm$^2$, preferentially 0.6 $10^5$ cells/cm$^2$) in 700 μL of Coculture 1% medium.

At least 4 hours later: discard the medium from the insert to switch to the ALI. Overnight incubation.

Figure 1:
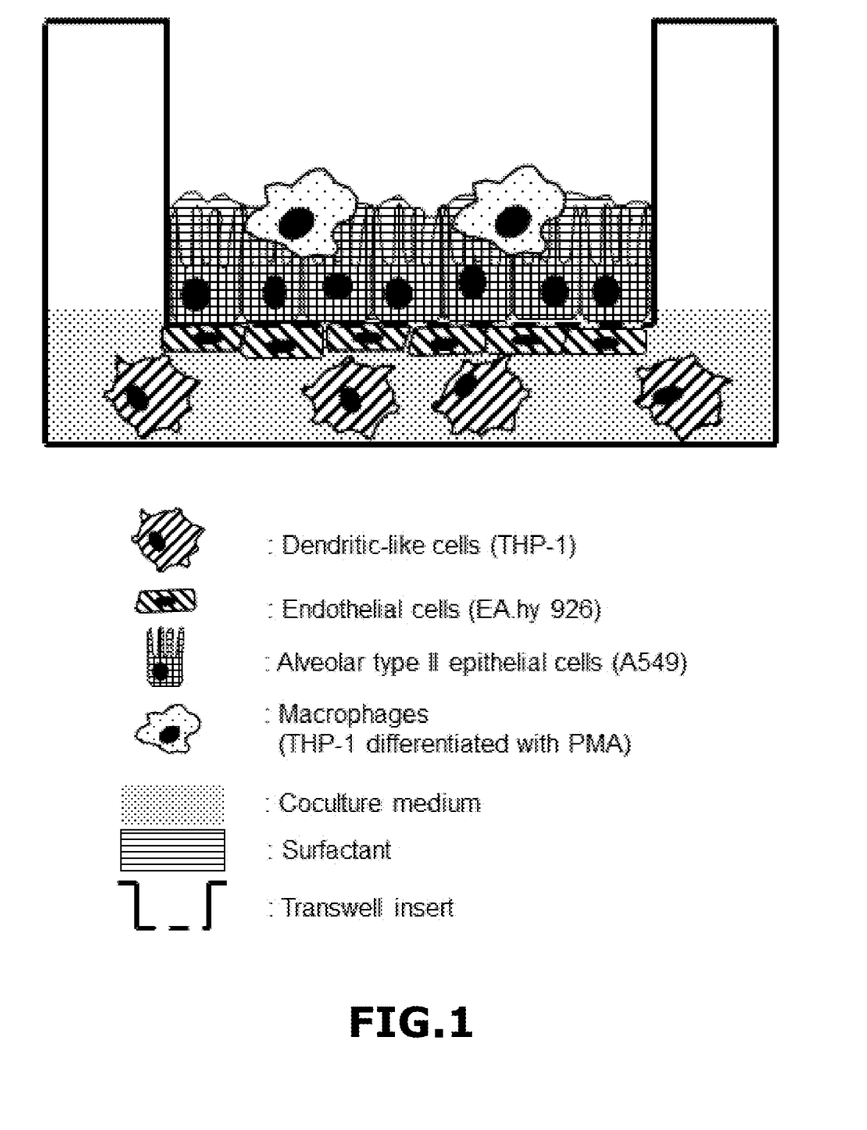
FIG. 1: is a schematic drawing of the Transwell® insert with the tetraculture of the present invention representing the lung model.
Figure 2A:
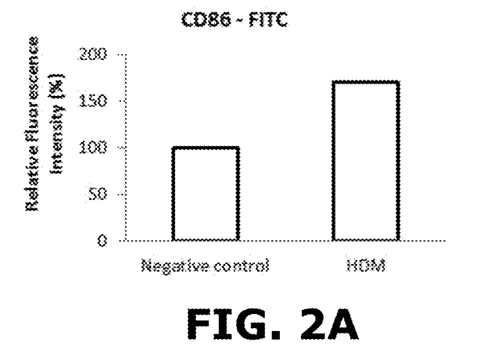
FIGS. 2A to 2E are histograms showing the expression of the respective cell surface markers CD86, CD40, IL7ra, CD54 and OX40L on the cell surface of THP-1 cells in the tetraculture lung model after 24 h exposure to HDM.
Figure 2B:
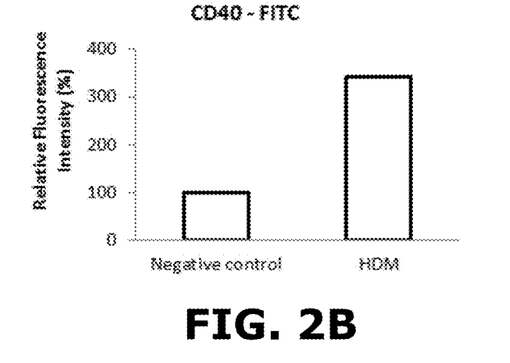
Figure 2C:
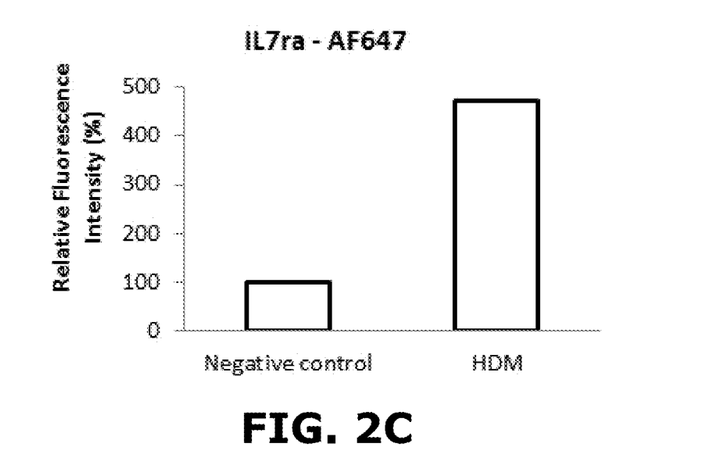
Figure 2D:
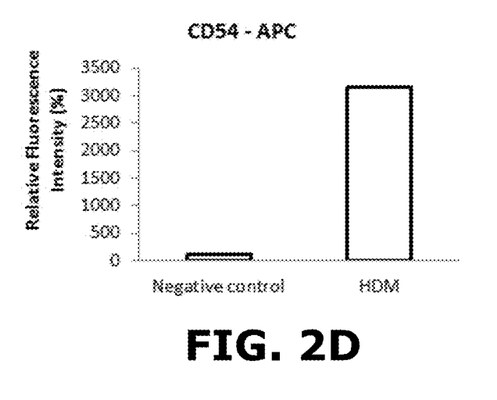
Figure 2E:
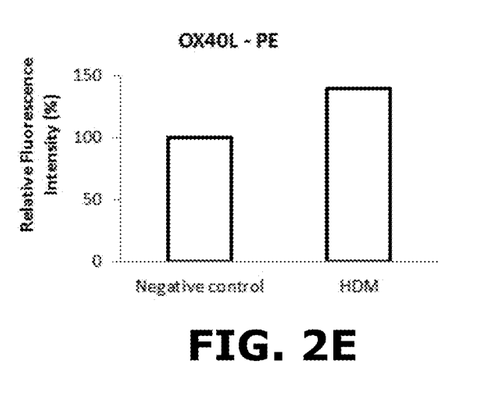

Exposure of the insert to the inhalable product (particles or molecules) to be tested on the three-dimensional model of the invention, prepared under the above protocol, can be performed after 10 to 12 hours (time required for the cells to produce the surfactant) with the in vitro lung model as presented on FIG. 1.

5. Day 5:

Example of exposure of the inserts is performed in a Vitrocell® Cloud device (Waldkirch, Germany), previously cleaned under sterile conditions, and maintained at 37° C. The inserts are placed into the device. A cloud, from 200 to 500 μL of the product to be tested) is then distributed homogenously inside the chamber and starts to settle on the surface. After about 10 to 30 minutes (depending on the injected product), the cloud is settled by single droplet sedimentation. The concentration which is deposited on the insert can be calculated in g/cm$^2$.

After exposure, the inserts are moved back to their plate and, after incubation (usually 24 h or 48 h depending of the compound to test, the following measurements can be performed.

6. Day 5, 6 or 7: Measurements

The biological endpoints from 0 to 48 h after exposure depending on the expected time- and end-points can be performed.

The possible biological endpoints to be measured are for instance: Cell viability or cytotoxicity, Cytokines secretion, DC migration, DC activation, Macrophages phagocytosis, EC activation, Macrophages phagocytosis, Staining for immune-cytochemistry or immune-fluorescence, or RNA extraction. This list is not limitative.

7. Day 5: Example of DC Isolation and Coculture with T-Cells

DC Isolation Using:

Cell sorting using FACS (e.g. BD FACS Aria) by using different markers required for T cells activation such as MHCII, CD86, CD54 (to recover activated THP-1 cells) and CD11a (to isolate cells from EA.hy.926 cells). It could be necessary to pool different wells in order to have enough cells for the coculture with T-cells.

Magnetic beads (e.g. Dynabeads) with positive or negative isolation with different surface markers such as MHCII, CD86, CD54 and CD11a.

Activated DC Coculture with T-Cells:

T-cells should present surface markers allowing the cell activation (TCR and CD4), survival (CD28 binding B7.1 or CD80 and B7.2 or CD86) and differentiation, Coculture cells in media:
  Coculture with 1% FBS (used for exposure of the tetraculture-DC)
  or RPMI 1640 with 10% FBS (used for both THP-1 and T-cell line)
  The addition of several compounds (such as cytokines needed for T cells differentiation . . . ) to mimic the complex tissue environment of the Secondary Lymphoid Organ has to be considered.

Cell ratio: several cellular ratios have been tested as only a few naïve T cells are able to recognize any given epitope (1 in $10^6$). DC should interact with many T cells in the hope of being found by a T cell that recognize in the antigen on its surface:
  0.01 million DC for 0.1 million T cells (1/10)
  0.01 million DC for 1 million T cells (1/100)
  0.01 million DC for 10 million T cells (1/1000)

Depending on the selected T cell line, medium should be either renewed or complemented by adding fresh medium (20% to 30% of volume every 2 or 3 days) following ATCC/supplier subculturing recommendations.

Endpoints Measurements:

Cytokines secretion (IL-4, IL-5 and IL-13) and surface marker expression should be measured every 24 h, from 24 h (1 day) coculture to 120 h (5 days) coculture. T-cells should present a Helper type 2 (TH2) profile if the compounds are a respiratory sensitizer.

Example 2

Inserts prepared according to example 1 were exposed to chemical compounds and to positive controls using the Vitrocell® Cloud system (Vitrocell, Waldkirch, Germany). All compounds were diluted in a 1/1(v/v) solution of sterile saline solution and PBS.

Exposure to HDM (House Dust Mite):

House dust mite is a very common allergen which is associated with asthma and allergic rhinitis. As no data were found for in vitro exposure, concentration to which cells of the lung model of the present invention were to be exposed was determined on the basis of in vivo studies. In vivo, mice are generally exposed intra-nasally to 1 pg of Der p1 (major protein allergen of HDM). Knowing that the alveolar surface of mice is 82.2 cm², a concentration of 0.01 µg/cm2 was calculated to expose to the insert (being 45 pg/insert).

Exposure to Chemicals:

Inserts were exposed to a range of concentrations to chemical respiratory irritants and sensitizers in order to determine first the viability of the tissue using the Alamar Blue assay. Resazurin, the active ingredient of Alamar Blue assay, is a cell permeable blue non-fluorescent compound. Upon entering cells, resazurin is reduced to pink highly fluorescent resorufin. Viable cells continuously convert resazurin to resorufin. The fluorescence is proportional to cell viability.

Following 24 h and 48 h exposure to the compounds through the Vitrocell cloud, cells were incubated for 1 hour to 400 µM of Alamar Blue diluted in Coculture 1% medium.

Once cell viability was determined for each compound, a concentration around 75% of viability was selected for the measurement of the expression of cell surface markers on THP-1 DC.

The tetraculture lung model was exposed to several concentrations of two known chemical respiratory sensitizers: Phthalic Anhydrid (PA) or Trimellitic Anhydride (TMA) and two known respiratory irritants: Acrolein (Acr), Methyl Salicylate (MeSa), or Sodium Dodecyl Sulfate (SDS).

Flow Cytometry Measurements:

24 h and 48 h after exposure to the Vitrocell Cloud, THP-1 DC were recovered in the medium in the well. After centrifugation for 5 minutes at 300 g, cells were washed with PBS and staining was performed using antibodies listed in table 1 below (following the manufacturer's recommended dilutions) and the corresponding isotype control to determine the unspecific binding of the antibody and ensure the observed staining is due to specific binding rather than an artifact.

TABLE 1

| Sensitization | | | |
|---|---|---|---|
| Surface Marker | Antibody | Excitation (nm) | Emission (nm) |
| TSLPr | APC mouse IgG1 (Biolegend) | 645 | 660 |
| OX40L | PE mouse IgG1 k anti-human OX40L (BD) | 496 | 578 |
| IL-7Ra | Alexa Fluor 647 mouse IgG1 (Biolegend) | 650 | 668 |
| CD86 | PE mouse IgG1 (BD) | 496 | 578 |
| CD54 | APC mouse IgG1 (BD) | 645 | 660 |
| CD40 | FITC mouse IgG1 (BD) | 493 | 525 |

For Cytotoxicity:

With SYTOX Blue the excitation wavelength is 444 nm, and the emission wavelength is 480.

Relative Fluorescence Intensity (RFI) was used as an indicator of OX40L, IL7ra, CD40 and CD86 and CD54 expression and was calculated by the following formula I:

$$RFI(\%) = \frac{MFI \text{ of treated cells} - MFI \text{ of treated isotype control cells}}{MFI \text{ of vehicle control cells} - MFI \text{ of vehicle isotype control cells}} \times 100$$

FIGS. 2A to 2E show respectively the expression of the cell surface markers CD86, CD40, IL7ra, CD54 and OX40L on the cell surface of THP-1 cells in the tetraculture lung model after 24 h exposure to HDM. Expression of the cell surface markers on the viable cells was measured via flow cytometry.

It is observed that all markers are upregulated after 24 h exposure to HDM compared to the control. Therefore, the markers IL7ra, OX40L, CD86, CD40, and CD54 on the cell surface of THP-1 cells in the tetraculture lung model could be used to determine the respiratory sensitization potential of chemical compounds.

Figure 3A:
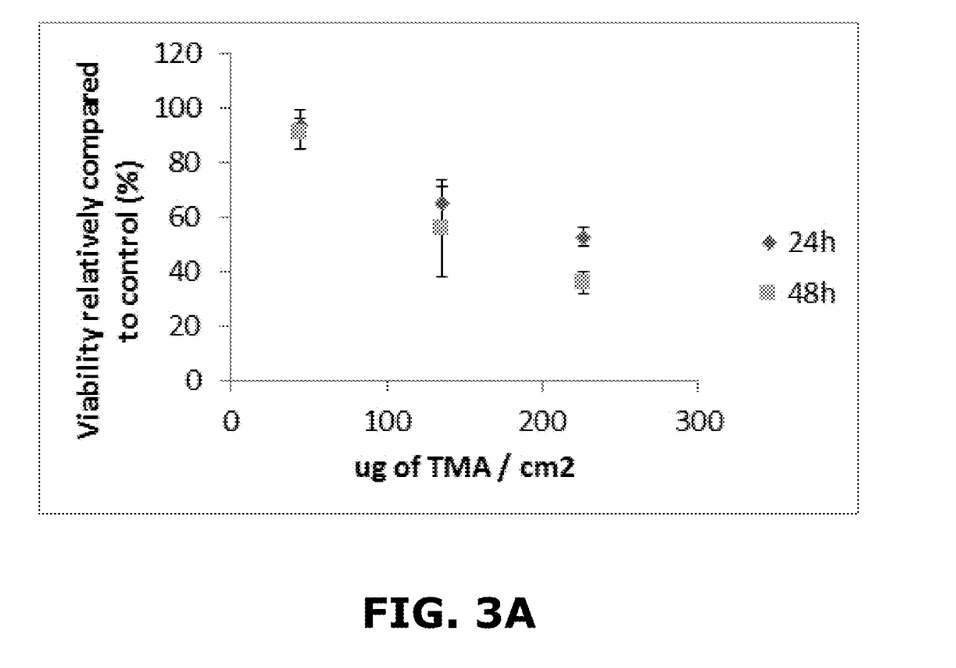
FIGS. 3A and 3B are diagrams presenting the viability % after 24 h and 48 h exposure to different concentrations of chemical respiratory sensitizers, respectively Trimellitic Anhydride (TMA) and Phthalic Anhydrid (PA)
Figure 3B:
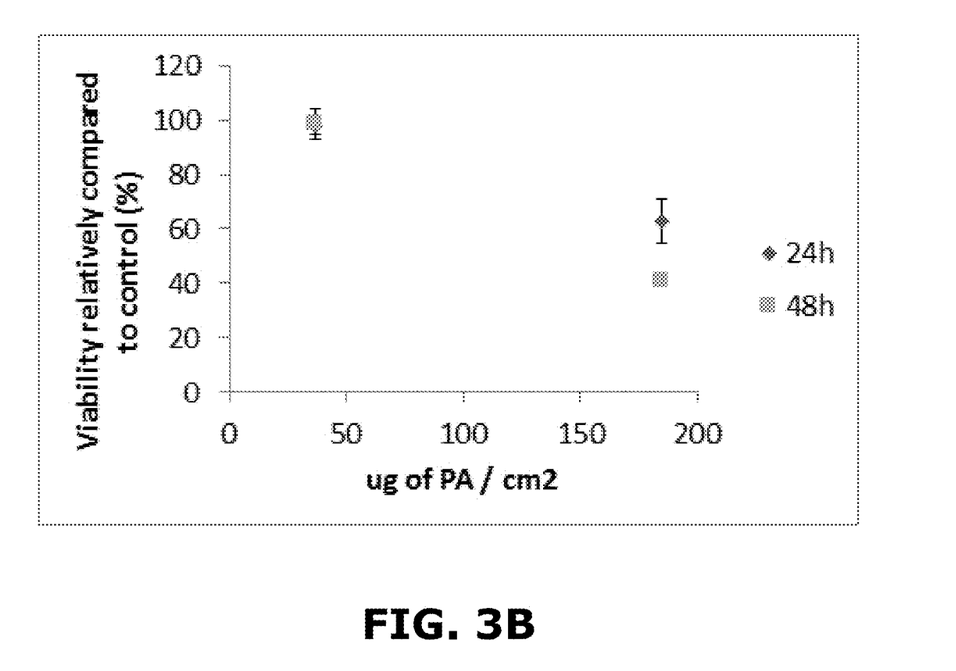

The diagrams of FIGS. 3A and 3B show the viability after 24 h and 48 h exposure to different concentrations of chemical respiratory sensitizers, respectively Trimellitic Anhydride (TMA) and Phthalic Anhydrid (PA).

A dose response is observed for cell viability of the alveolar tissue model.

Figure 4A:
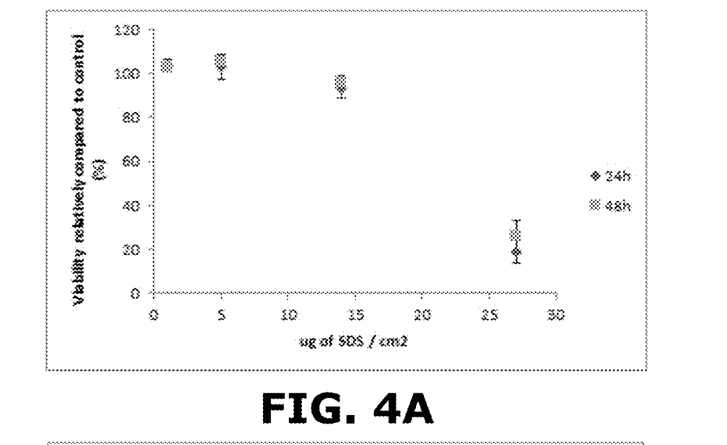
FIGS. 4A, 4B and 4C are diagrams showing the viability % after 24 h and 48 h exposure to different concentrations of chemical respiratory irritants, respectively Sodium Dodecyl Sulfate (SDS), Acrolein (Acr) and Methyl Salicylate (MeSa)
Figure 4B:
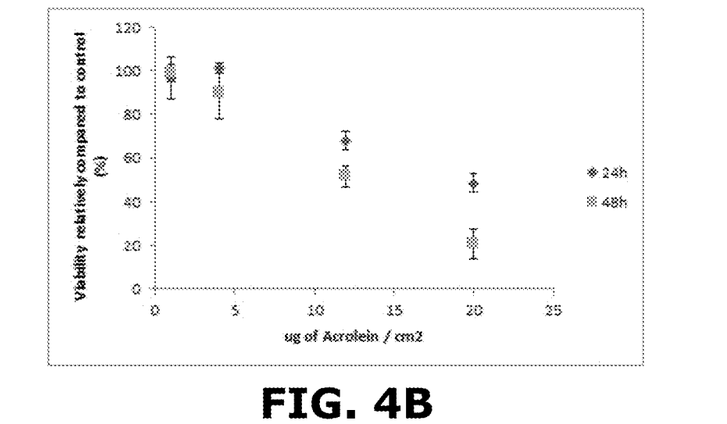
Figure 4C:
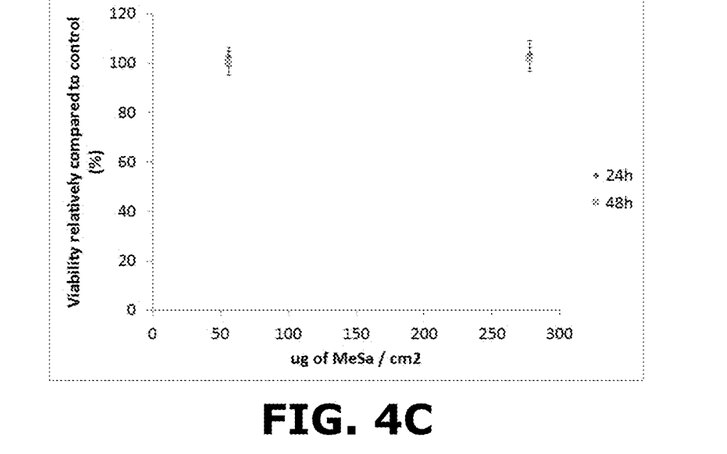

The diagrams of FIGS. 4A, 4B and 4C show the viability after 24 h and 48 h exposure to different concentrations of chemical respiratory irritants, respectively Sodium Dodecyl Sulfate (SDS) and Acrolein (Acr) and Methyl Salicylate (MeSa).

A dose response is also observed for cell viability of the alveolar tissue model.

Example 3

The Vitrocell® Cloud system (Vitrocell, Waldkirch, Germany) was used for the delivery and exposure of cells to nebulize the compounds diluted in PBS and depending on the vehicle control, in sterile water or sterile water plus DMSO.

House Dust Mites (HDM), protein Bet v1 (an additional known protein sensitizer) and Acrolein (Acr) were diluted in sterile water. Phthalic anhydride (PA), Trimellitic anhydride (TMA) and Methyl salicylate (MeSa) were diluted in DMSO.

Viability was assessed using the Alamar Blue assay 24 h and 48 h after exposure according to the protocol detailed in example 2 above.

The concentration leading to 25% of cytotoxicity (meaning 75% of viability: CV75) relatively compared to the vehicle control was determined using the graphs presented in example 2.

To measure the expression of cell surface markers and the release of different cytokines, the cells of inserts prepared according to example 1 above were exposed to the CV75 or, when it was not possible to reach 75% of viability, cells were exposed to the maximum of solubility of the compounds.

Bet v1 Exposure:

As no data were found for in vitro exposure, concentration to which cells of the lung model of the present invention were to be exposed was determined on the basis of in vivo studies. In vivo, mice were exposed to 2 pg of bet v1 (important protein allergen of pollen). Knowing that the alveolar surface of mice is 82.2 cm$^2$, a concentration of 0.024 pg/cm2 was calculated.

After 24 h and 48 h, THP-1 cells were recovered, stained and analysed using a flow cytometer according to the protocol detailed in example 2 above. Supernatants were recovered for cytokines measurements.

No effect on viability was observed after exposure to HDM and Bet v1.

Exposure to Bet v1 led to a viability relatively compared to control of 100.7%+/−1.2% at 24 h and 89.5%+/−4.2% at 48 h. Exposure to HDM led to a viability relatively compared to control of 100.0%+/−0.03% at 24 h and 95.7%+/−0.03% at 48 h.

In parallel, THP-1 cells were exposed in submerged conditions in monoculture in order to reproduce the data obtained using the h-CLAT (human cell line activation test) assay. The h-CLAT assay is based on the property of chemicals to activate dendritic cells, property which is common to both skin and respiratory sensitizers. The h-CLAT is an in vitro model validated at the European level (ECVAM validation).

On a comparative purpose, the expression of CD86 and CD54 cell surface markers were also evaluated in the h-CLAT. It is currently recommended to use the h-CLAT to assess the skin sensitizing potential of chemicals. As skin and lung share the DC activation property, h-CLAT may be considered to be used to assess also the respiratory sensitizing potential of chemicals. To remind, there is no validated models to assess respiratory sensitization available on the market yet.

As different antibodies, fluorochromes and equipment were used to measure the CDs expression, threshold level obtained in literature on the h-CLAT could not be compared to those measured in this example.

Figure 5A:
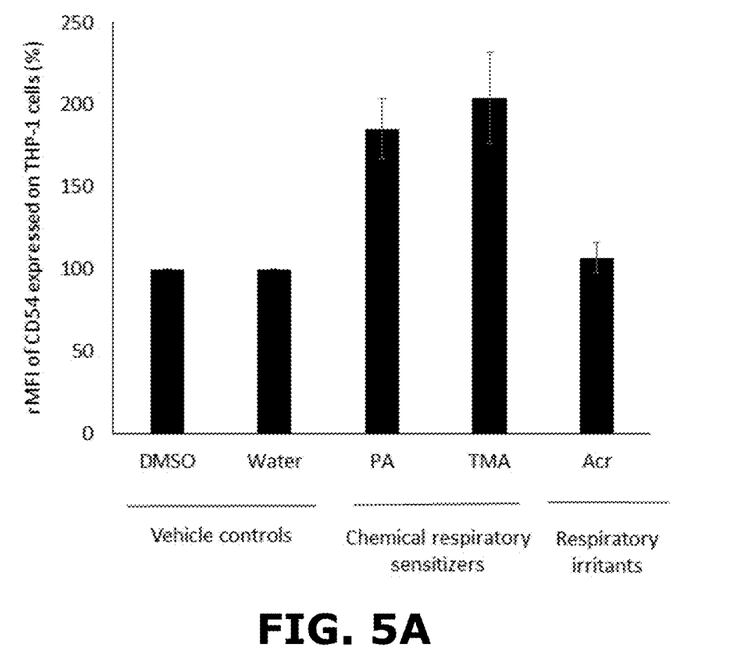
FIGS. 5A and 5B are diagrams showing the cell surface marker expression of CD54 on THP-1 cells in the tetraculture in vitro lung model according to the invention (A), and in monoculture model not forming part of the invention (B) after exposure to sensitizers and irritants for 24 h (mean+/−standard error)
Figure 5B:
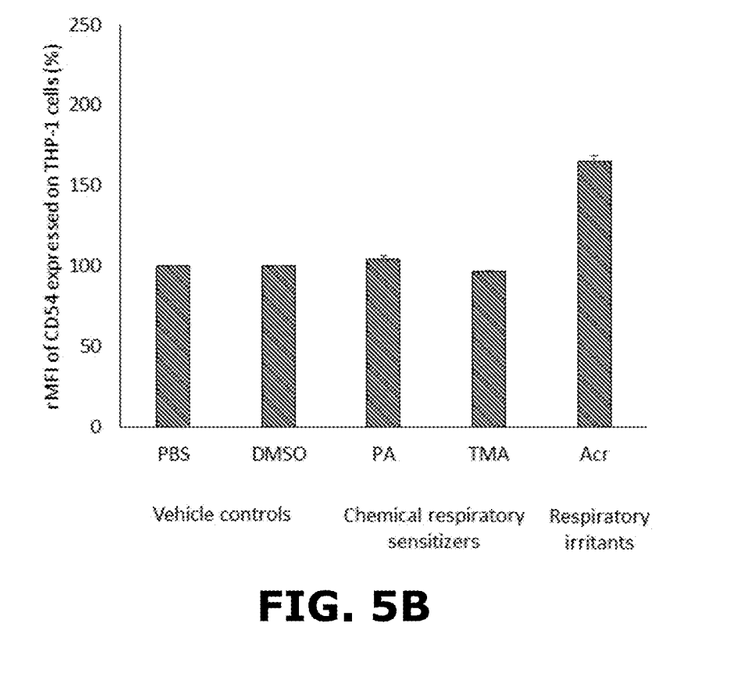

However, FIG. 5 shows the expression of CD54 on THP-1 cells in tetraculture (A) and in monoculture (B). Increases were observed after the exposure to chemical respiratory irritants (PA and TMA) whereas no increase was observed for vehicle controls (water and DMSO) and the chemical irritant (acrolein) (FIG. 5A). On the contrary in FIG. 5B, no increase was observed in monoculture after exposure to respiratory sensitizers and increase of CD54 expression was measured after exposure to the irritant which misclassifying the irritant chemical acrolein as sensitizer.

Figure 6A:
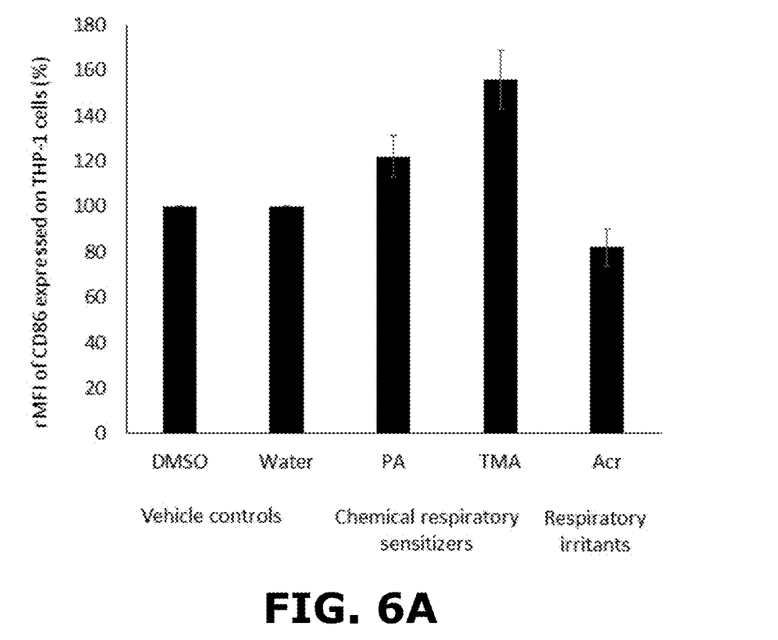
FIGS. 6A and 6B are diagrams showing the cell surface marker expression of CD86 on THP-1 cells in the tetraculture in vitro lung model according to the invention (A), and in a monoculture model not forming part of the invention (B) after exposure to sensitizers and irritants for 24 h (mean+/−standard error)
Figure 6B:
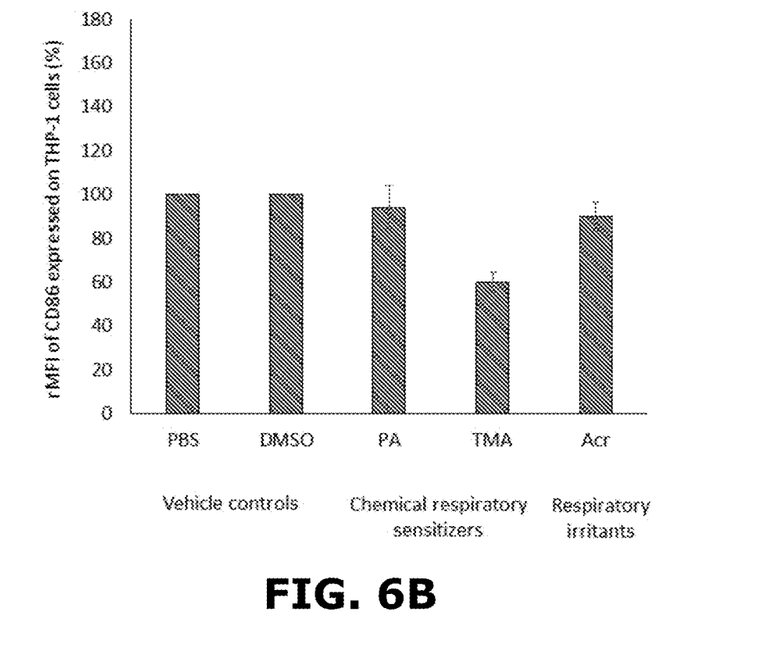

FIG. 6 shows the expression of CD86 on THP-1 cells in tetraculture (A) and in monoculture (B). Increases were observed after the exposure to chemical respiratory irritants (PA and TMA) whereas no increase was observed for vehicle controls (water and DMSO) and the chemical irritant (acrolein) (FIG. 6A). On the contrary, no increase was observed in monoculture after exposure to respiratory sensitizers and the CD86 expression after TMA exposure is even lower than the vehicle control (FIG. 6B).

The three-dimensional in vitro alveolar lung model according to the present invention (tetraculture) shows then an improvement for the discrimination of chemical respiratory sensitizers and irritants. To reinforce the discriminating property of the system, additional markers were used and respiratory protein sensitizers were also added to the set of tested compounds.

Figure 7:
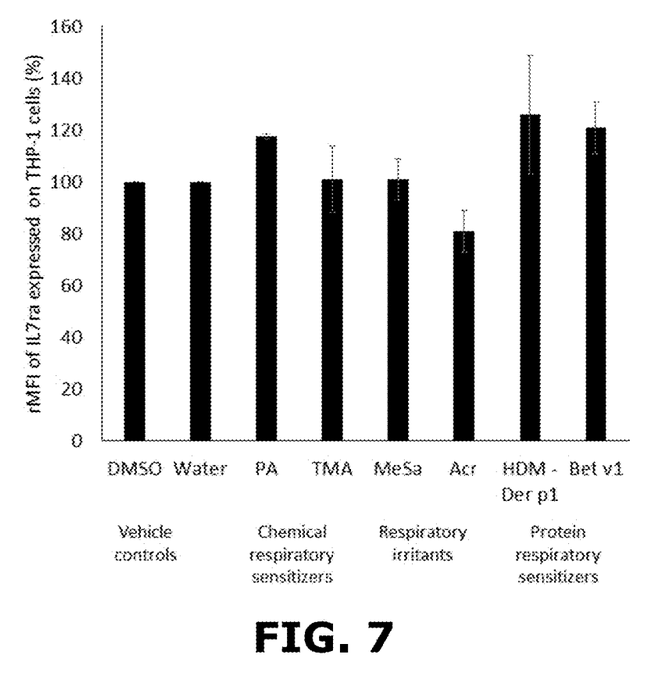
FIG. 7 is a diagram showing the cell surface marker expression of ILra on THP-1 cells in the tetraculture in vitro lung model according to the invention after exposure to sensitizers and irritants for 24 h (mean+/−standard error)

FIG. 7 shows the cell surface marker expression of IL7ra on THP-1 cells in the tetraculture after exposure to sensitizers and irritants for 24 h. The decrease of IL7ra expression after acrolein exposure could be used as a discriminating marker between irritants and sensitizers (regardless of types, chemical or protein).

Figure 8:
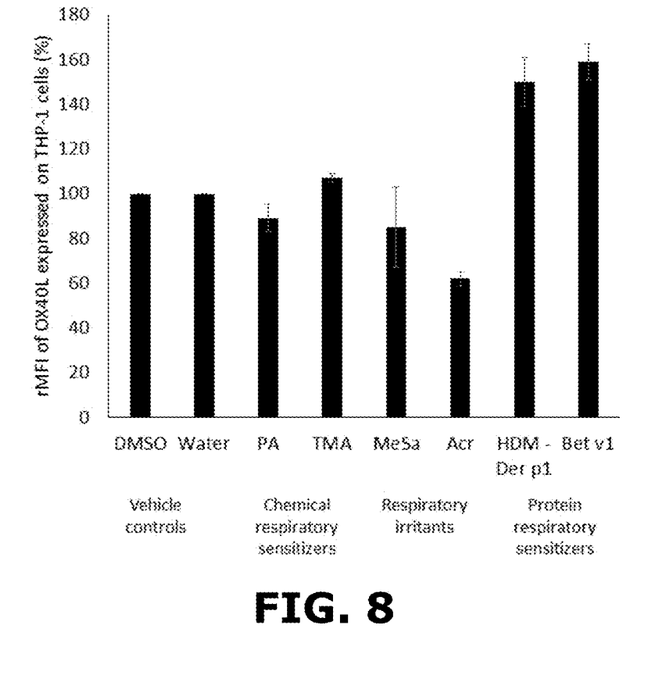
FIG. 8 is a diagram showing the cell surface marker expression of OX40L on THP-1 cells in the tetraculture in vitro lung model according to the invention after exposure to sensitizers and irritants for 24 h (mean+/−standard error)

FIG. 8 shows the cell surface marker expression of OX40L on THP-1 cells in the tetraculture after exposure to sensitizers and irritants for 24 h. The increase of OX40L expression after protein sensitizers exposure could be used as a discriminating marker between protein sensitizers and the chemical irritants/sensitizers.

Figure 9:
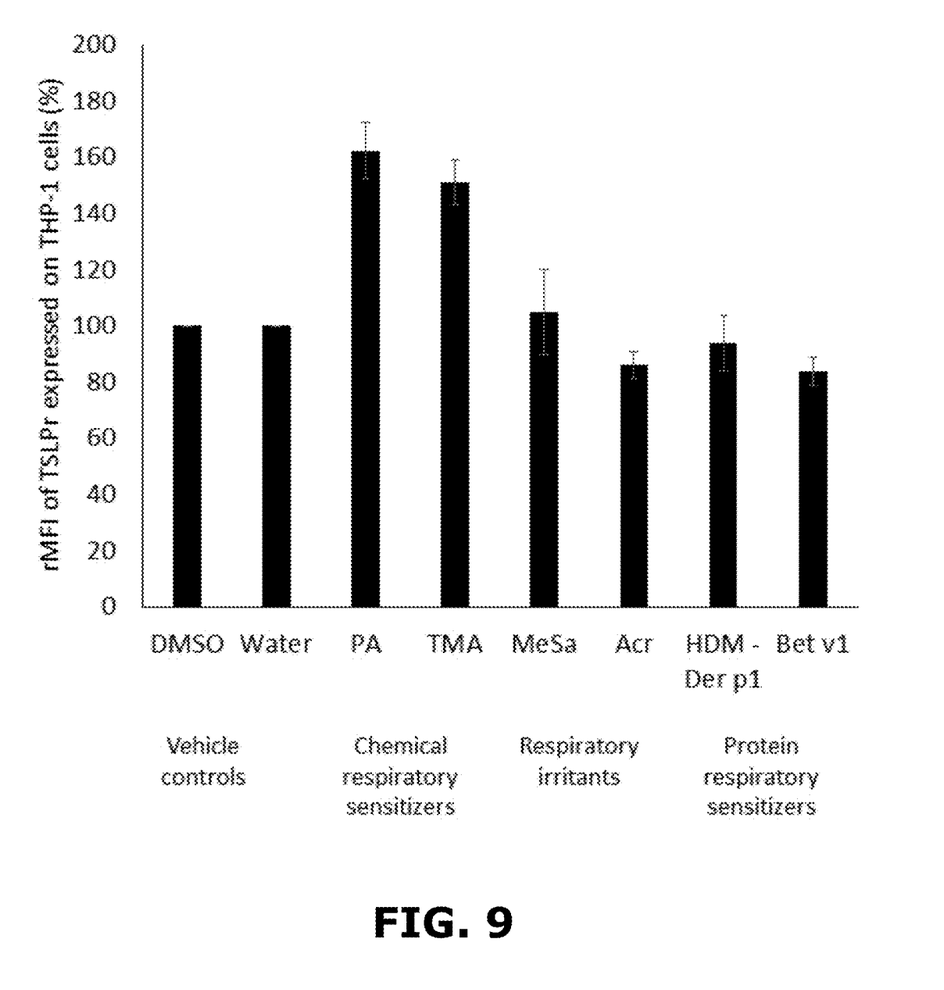
FIG. 9 is a diagram showing the cell surface marker expression of TSLPr on THP-1 cells in the tetraculture in vitro lung model according to the invention after exposure to sensitizers and irritants for 24 h (mean+/−standard error)

FIG. 9 shows the cell surface marker expression of TSLPr on THP-1 cells in the tetraculture after exposure to sensitizers and irritants for 24 h. The increase of TSLPr expression after chemical sensitizers exposure could be used as a discriminating marker between chemical sensitizers and the chemical irritants/protein sensitizers.

Other parameters were evaluated in the system after the exposure of acrolein and both chemical respiratory sensitizers PA and TMA.

Table 2 below gives a summary of the results obtained for all cytokines measured, wherein, ↘ indicates a decrease of cytokine release compared to the vehicle control, ↗ indicates an increase of cytokine release compared to the vehicle control and =indicates no change observed between exposure and the vehicle control:

TABLE 2

|  | Acrolein | | PA | | TMA | |
| --- | --- | --- | --- | --- | --- | --- |
|  | 24 h | 48 h | 24 h | 48 h | 24 h | 48 h |
| MCP-1 | ↘ | = | = | ↗ | = | = |
| MIP-3a | ↘ | ↘ | ↗ | ↗ | ↗ | ↗ |

TABLE 2-continued

|  | Acrolein | | PA | | TMA | |
| --- | --- | --- | --- | --- | --- | --- |
|  | 24 h | 48 h | 24 h | 48 h | 24 h | 48 h |
| IL-6 | ↘ | ↘ | ↗ | ↗ | ↗ | ↗ |
| IL-7 | ↗ | ↗ | = | = | = | = |
| RANTES | = | ↗ | ↗ | ↗ | ↗ | ↗ |
| GM-CSF | ↘ | ↘ | ↗ | ↗ | ↗ | ↗ |
| IL-10 | ↘ | ↘ | ↗ | ↗ | ↗ | = |

Figure 10A:
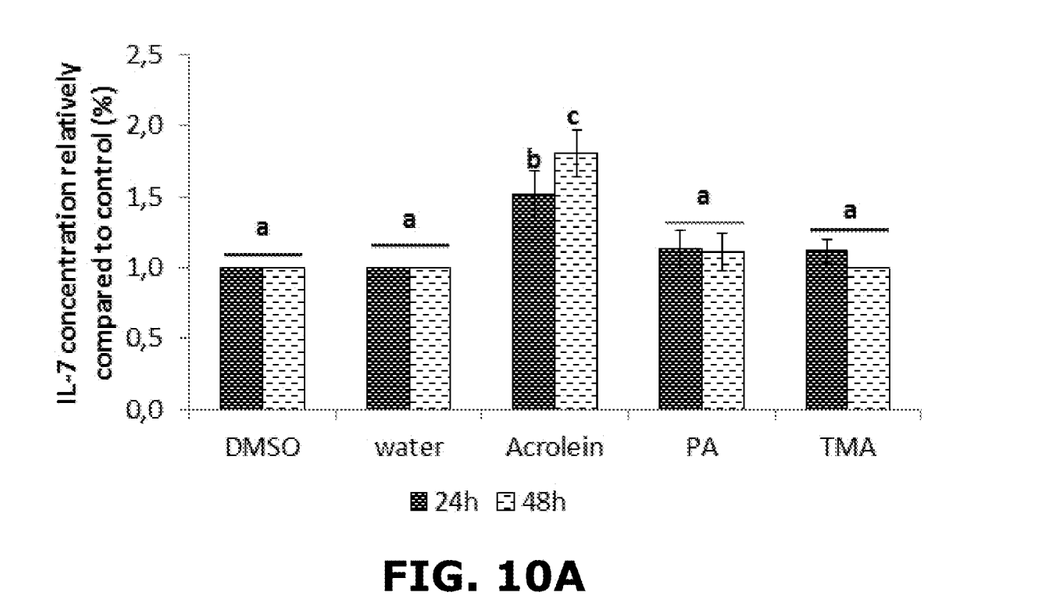
FIGS. 10A and 10B are diagrams showing cytokines released in the tetraculture in vitro lung model according to the invention after exposure to chemical sensitizers and irritants for 24 h and 48 h (A): IL-7 basal levels: DMSO basal level for 24 h: 18.2±0.0 pg/mL; for 48 h: 19.5±1.2 pg/mL; Water for 24 h: 18.6±0.3 pg/mL; for 48 h: 18.2±0.0 pg/mL (B) GM-CSF basal levels: DMSO basal level: DMSO: for 24 h: 32.4±6.0 pg/mL; for 48 h: 31.0±3.7 pg/mL; water: for 24 h: 47.0±9.2 pg/mL; for 48 h: 43.1±5.4 pg/mL (Mean+/−SE) (Letters illustrate significant differences (Factorial ANOVA+Fisher LSD post hoc test at $P<0.05$ level of significance, n=6).
Figure 10B:
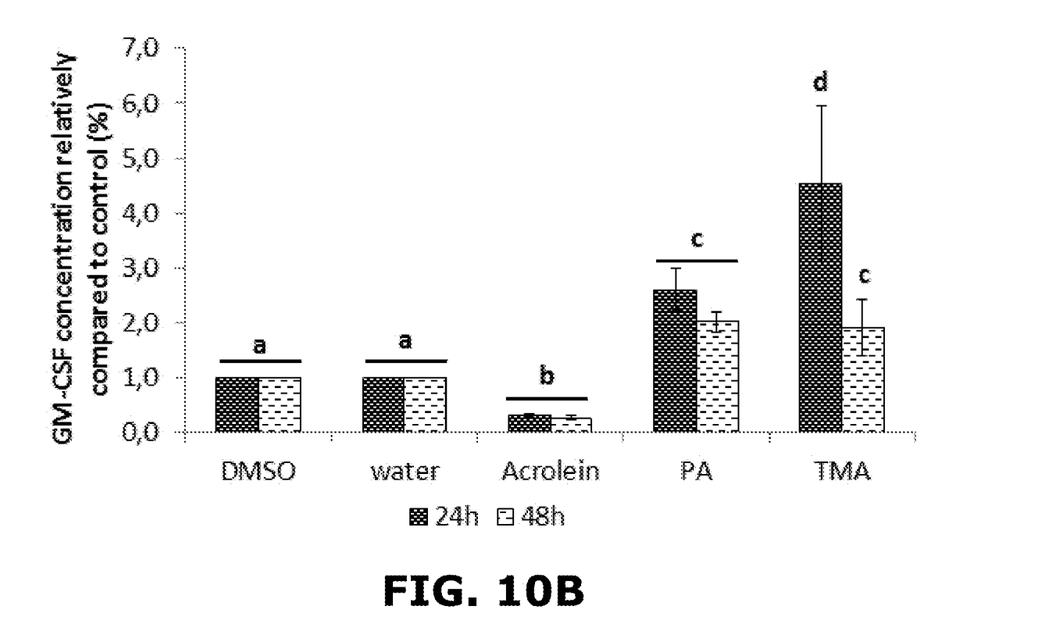

These results are also illustrated in FIG. 10 which gives more insights of IL-7 (FIG. 10A) and GM-CSF (FIG. 10B) concentrations relatively compared to vehicle controls. Increase of MCP-1, MIP-3a, IL-6 RANTES, GM-CSF and IL-10 release could be used as markers for respiratory sensitizers. The decrease of MCP-1, MIP-3a, IL-6, GM-CSF and IL-10 release could be used as markers for respiratory irritants along with the increase of IL-7 cytokine release.

Figure 11A:
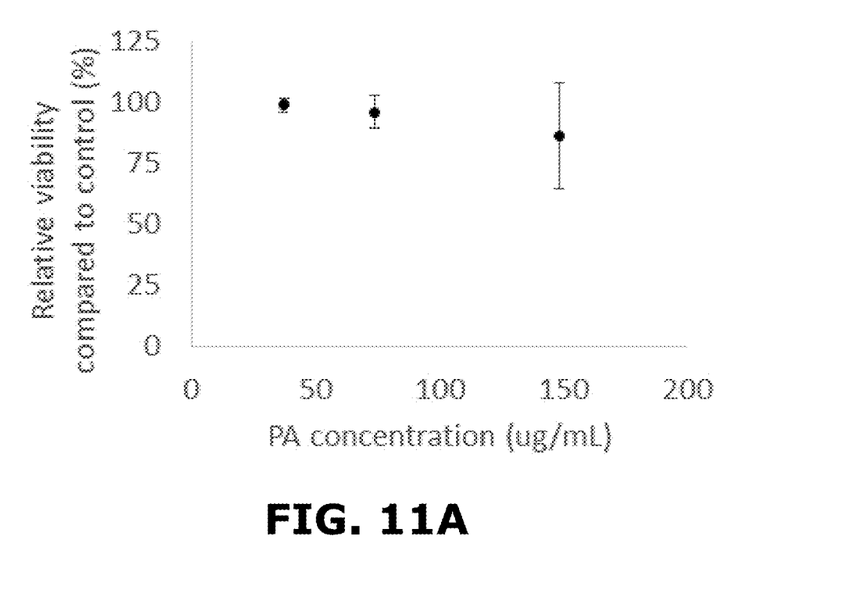
FIGS. 11A and 11B are diagrams showing viability of THP-1 cells after 24 h exposure to PA (FIG. 11A) and TMA (FIG. 11B) in monoculture in submerged conditions. In this figure, the highest tested concentrations represent the maximum of solubility of the compounds in medium containing 0.2% of DMSO.
Figure 11B:
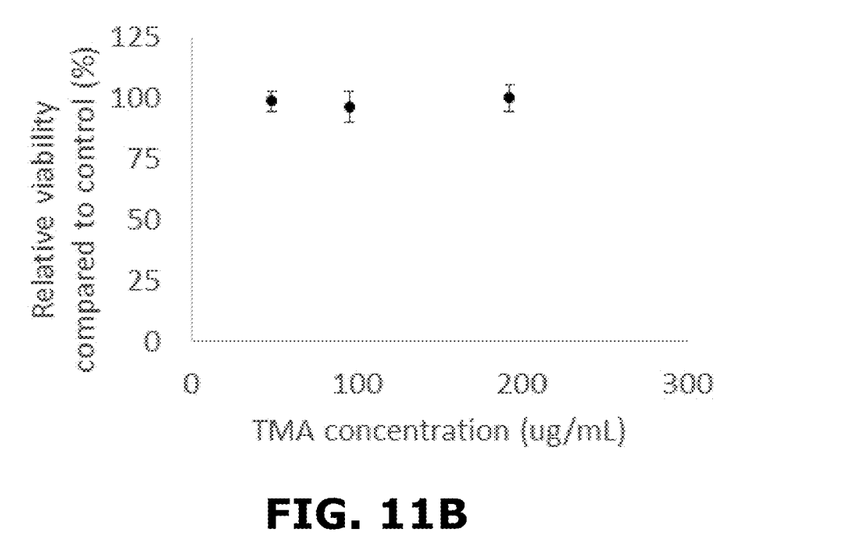

Finally, and as shown on FIG. 11, it has to be noted that due to the low solubility of TMA and PA, it is not possible to reach any cytotoxity of THP-1 cells in monoculture in submerged conditions (FIGS. 11A and 11B) while decrease in viability is observed in the tetraculture system after exposure to these compounds (FIGS. 3A and 3B).

While only certain features of the invention have been illustrated and described herein, many modifications, substitutions, changes or equivalents will now occur to those skilled in the art. It is therefore, to be understood that this application is intended to cover all such modifications and changes that fall within the true spirit of the invention.

The invention claimed is:

1. A three-dimensional in vitro alveolar lung model comprising:
   without mast cells, the four cells types as follows:
   a) alveolar type II epithelial cells able to secrete surfactant,
   b) endothelial cells which form the inner lining of capillaries providing a permeable barrier
   c) dendritic-like cells,
   d) macrophage-like cells, able to participate to defense mechanisms by ingesting foreign materials by phagocytosis, wherein:
   said three-dimensional in vitro lung model is in the form of a culture well equipped with a porous membrane separating the well into an apical compartment exposed to an air-liquid interface, and a basolateral compartment submerged in a culture medium, said epithelial cells and said macrophages being present in the apical compartment, and said endothelial cells and said dendritic-like cells being present at the basolateral compartment and immerged in the culture medium,
   said porous membrane has pores comprised between 2 and 10 μm, dimensioned to allow migration of the dendritic-like cells from the basolateral compartment to the apical compartment.

2. The model according to claim 1 wherein said macrophage-like cells are THP-1 cells, differentiated with either one of PMA (Phorbol-12-myristate-13-acetate) or with 1,25-dihydroxyvitamin D3.

3. The model according to claim 1, wherein all cells are immortalized human cell lines.

4. The model according to claim 1, wherein said alveolar type II epithelial cells are A549 cells.

5. The model according to claim 1, wherein said endothelial cells are EA.hy926 cells.

6. The model according to claim 1, wherein said dendritic-like cells are non-differentiated THP-1 cells.

7. The model according to claim 1, wherein the porous membrane has pores comprised between 3 and 8 μm.

8. A process for preparing the three-dimensional in vitro alveolar lung model as defined in claim 1, comprising:
   co-culturing of cells a)-d) in a culture well equipped with an insert having a porous membrane that separates the apical and the basolateral compartments of said culture well, in the following step sequence:
   i) seeding the lower face of a membrane insert having pores between 2 and 10 μm, with $0.24 \times 10^5$ to $0.6 \times 10^5$ endothelial cells/cm$^2$, said lower face corresponding to the basolateral side,
   ii) at least four hours later, seeding the other side of the membrane insert with the alveolar type II epithelial cells, said other side of the membrane insert corresponding to the apical side,
   iii) about 4 days later, adding a cell suspension containing between 0.1 and one million dendritic-like cells/mL to the lower basolateral side of the membrane insert, and then
   iv) adding macrophage-like cells on top of the alveolar type II epithelial cells seed, and finally,
   v) introducing the membrane insert into a co-culture medium in order that said endothelial cells and said dendritic-like cells are present at the basolateral compartment and immerged in the co-culture medium; and said epithelial cells and said macrophages-like cells are present in the apical compartment, at the air-liquid interface.

9. The process according to claim 8, wherein at least one of said macrophage-like cells are THP-1 cells differentiated with PMA (Phorbol-12-myristate-13-acetate), said alveolar type II epithelial cells are A549 cells, said endothelial cells are EA.hy926 cells, or said dendritic-like cells are non-differentiated THP-1 cells.

10. The process according to claim 8, wherein, in the step ii) the other side of the membrane insert is seeded with the alveolar type II epithelial cells at a seeding density of $0.12 \times 10^5$ to $1.2 \times 10^5$/cm$^2$ cells.

11. The process according to claim 8, wherein, in the step ii) the other side of the membrane insert is seeded with the alveolar type II epithelial cells at a seeding density of $0.5 \times 10^5$ to $1.0 \times 10^5$/cm$^2$ cells.

12. The process according to claim 8, wherein, in the step iv) $0.12 \times 10^5$ to $1.2 \times 10^5$ macrophage-like cells/cm$^2$ are added on top of the alveolar type II epithelial cells.

13. A process for determining and/or predicting the sensitizing effects, and/or the irritation potential or toxicity of an inhalable product on the alveolar barrier of lungs, comprising:
   A) a step of exposing by pulverizing and nebulizing the inhalable product over the apical compartment of a three-dimensional in vitro alveolar lung model as defined in claim 1, wherein the porous membrane having pores comprised between 2 and 10 μm, and wherein exposing leads to activation of the dendritic-like cells, and
   B) a step of co-culturing said activated dendritic-like cells with a T lymphoblast cell line.

14. The process according to claim 13, wherein T-cells present a Helper type 2 (TH2) profile if the product to be tested is a suspected respiratory sensitizer.

15. The process according to claim 13, wherein markers for the respiratory sensitization potential are measured by FACS and/or by ELISA.

16. The process according to claim 15, wherein said markers for the respiratory sensitization measured by FACS are at least one of the following: CD40, CD54, CD86, TSLPr, IL-1ra, OX40L.

17. The process according to claim 15, wherein markers for the respiratory sensitization measured by ELISA are at least one of the following: TSLP, IL-33, IL-25, RANTES, MCP-1, MIP-3a, IL-6, IL-7, IL-10, GM-CSF.

18. The process according to claim 13, wherein further biological endpoints comprising release of interleukins, genotoxicity, biomarkers of sensitization, proteomics, transcriptomics and metabolic activation are measured.

* * * * *